United States Patent [19]
Golden

[11] 4,098,279
[45] Jul. 4, 1978

[54] THERAPEUTIC THERMAL PACK UNIT

[76] Inventor: Theodore Alan Golden, 1063 Ardmore, Birmingham, Mich. 48084

[21] Appl. No.: 783,815

[22] Filed: Apr. 1, 1977

[51] Int. Cl.² ............................................. A61F 7/00
[52] U.S. Cl. .................................................. 128/400
[58] Field of Search ............... 128/399, 400, 254, 258, 128/82.1; 150/2.1–2.4

[56] References Cited

U.S. PATENT DOCUMENTS

| | | | |
|---|---|---|---|
| 2,606,005 | 8/1952 | Poux | 128/258 |
| 3,714,947 | 2/1973 | Hardy | 128/400 |

FOREIGN PATENT DOCUMENTS

| | | | |
|---|---|---|---|
| 1,184,028 | 2/1959 | France | 128/400 |
| 1,262,837 | 4/1961 | France | 128/400 |

Primary Examiner—Lawrence W. Trapp
Attorney, Agent, or Firm—Cullen, Settle, Sloman & Cantor

[57] ABSTRACT

A pack unit or compress is formed in two halves each containing one or more channels and the halves are arranged face-to-face with a separator sheet covering the channels almost to their blind ends. The cold or, if desired, hot thermal fluid may flow through all of the channels in one of the halves simultaneously and then around the edge of the separator sheet in the blind ends of the channels and then through the channels of the opposite half to exit from the outlet end thereof. The unit may be appropriately contoured to closely fit a selected portion of the anatomy and can be used to continuously apply a uniformly cold compress to patients whose skin surfaces have recently undergone plastic surgery, skin grafting or the like to reduce swelling and to slow down the tendency of the newly-applied skin to die before the flow of blood begins. The non-serpentine flow path of the thermal fluid through the compress insures a relatively linear thermal gradient along the length of the pack and eliminates undesirable points of thermal discontinuity or thermal aberations.

10 Claims, 6 Drawing Figures

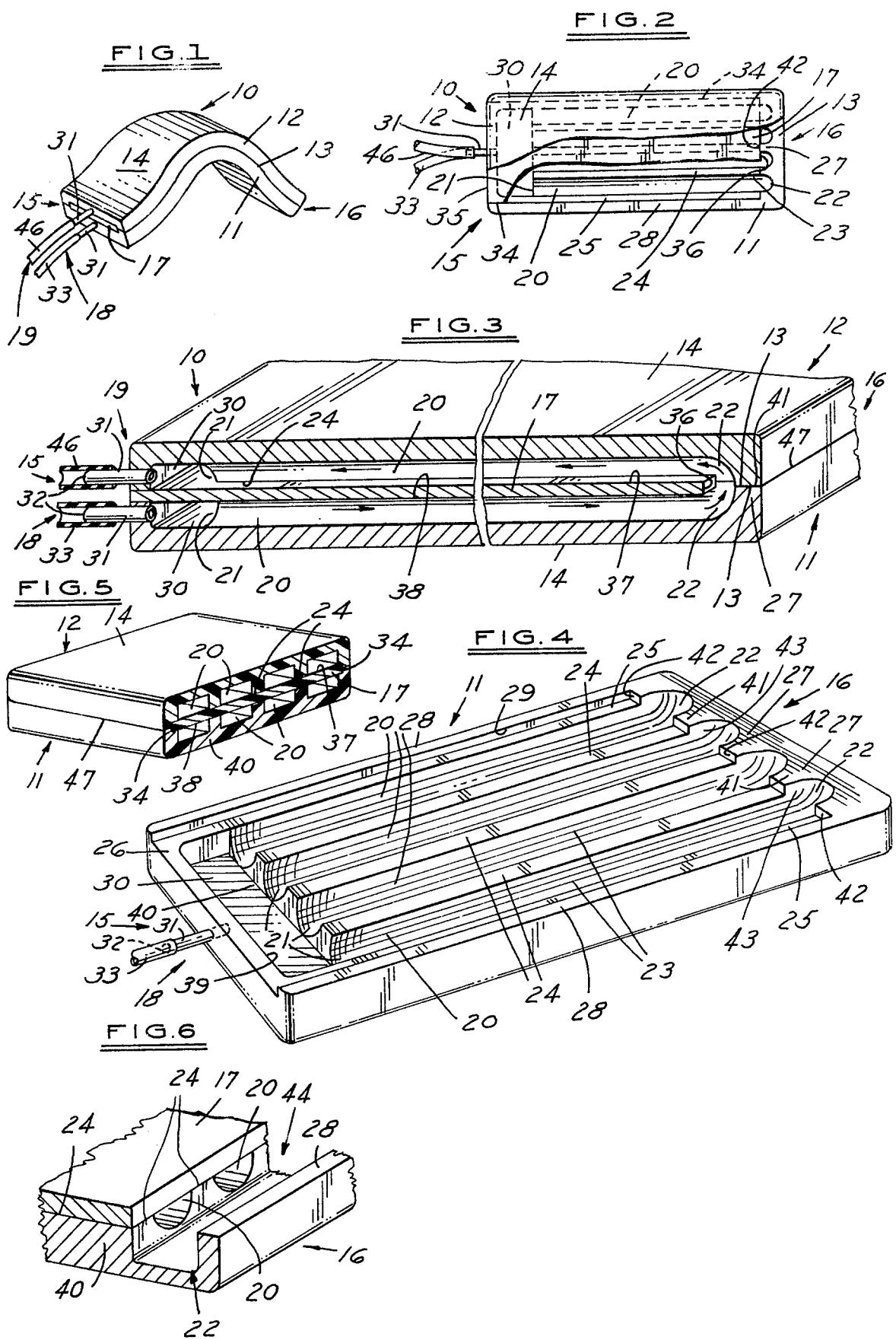

THERAPEUTIC THERMAL PACK UNIT

BACKGROUND OF THE INVENTION

The present invention relates to thermal packs or applicator units for making hot or cold applications to the human body in medical treatment, and more particularly, to a therapeutic thermal pack unit which can be contoured to a predetermined portion of a person's body for maintaining a uniform body temperature for therapeutic purposes.

A plurality of hot or cold applicators exist in the prior art whereby a thermal fluid is circulated at a first temperature from a supply into an applicator and thence through a serpentine or convoluted path back out of the applicator to return the circulating fluid to the supply so that a continuous flow of fluid at said first temperature may be inputted to the applicator. Such systems are shown in U.S. Pat. Nos. 1,896,953; 2,726,658; and 3,683,902 which are incorporated by reference herein for teaching systems in which such applicator units may be used and for teaching thermal fluid storage and circulation means for such systems.

Such systems do not, however, insure a uniform temperature throughout the system. In fact, the opposite is true. In the first place, cooling fluid tends to heat (and heating fluid tends to cool) as it travels along the serpentine or convoluted path. The further the fluid travels from the point of input the warmer (or cooler) it becomes. Due to the serpentine or convoluted nature of the fluid paths used in the prior art, one area may be cooled at a first temperature while another area immediately adjacent thereto may be at quite a different temperature since it may be directly under another portion of the fluid conduit which has traveled some distance and then returned adjacent the first portion. Such temperature discontinuities or differentials over a relatively slight distance are undesirable.

One of the prime objects of the compress of the present invention is to enable it to be readily configured to conform to any part of the human body which has recently undergone plastic surgery, a skin graft or the like, such as the area of the human body about an eye, a nose, an ear, or the like, and then to provide a relatively uniform and constant relatively cool temperature to such an area to prevent swelling and to retard the tendency of the newly-applied skin to die before the flow of blood begins.

It has been found that optimum results are often achieved when the temperature is maintained relatively constant or at least when a relatively constant linear temperature gradient is established along the length of the compress so that immediately adjacent areas do not experience relatively sharp temperature differentials.

The present invention eliminates the deficiencies of the prior art and provides a mechanically simple, low cost, therapeutic thermal pack unit or compress which can be molded to retainably conform closely to the contours of any given portion of the human body and which can simultaneously provide a constant or at least a uniform linear temperature gradient along the length of the pack unit thereby greatly enhancing its therapeutic value.

BRIEF SUMMARY OF THE INVENTION

The present invention provides a therapeutic thermal pack unit for maintaining a relatively constant temperature gradient over a predetermined area of the human body over which it is applied comprising a first and second pack unit section each having generally open interior sections adapted to be secured together in a fluid tight face-to-face manner. The first pack unit section includes a plurality of elongated substantially parallel channels, flat land portions about the channels and an input header means adjacent a first end of the channels for simultaneously supplying a thermal fluid to the channels for initiating fluid flow toward the opposite end thereof. A separator sheet means is adapted to be disposed upon the flat land portions so as to overlie substantially all of the channels from adjacent the header means to a point a predetermined distance from the opposite ends of the channels to seal the top of the channels except for the uncovered area immediately adjacent the opposite ends thereof. The second pack unit section includes an output header and channel means also sealed by the separater sheet means from adjacent the output header means to a predetermined distance from the opposite ends of the channels so that the thermal fluid fed into the input header and through the plurality of elongated channels of the first section passes around the opposite end of the separator sheet means and back through the channel means of the second section to the output header from whence it may be recirculated, if desired.

The present invention provides a relatively simple, easy-to-make and easy-to-use pack unit which readily conforms to various body surface areas and which will stay in place without constant external pressure. It is easily portable, disposable, and able to selectively heat or cool any desired portion of the human body for therapeutic purposes.

The present invention eliminates or minimizes thermal discontinuities or differences between adjacent areas and insures a relatively uniform or constant thermal gradient along the length of the therapeutic thermal pack unit.

Other advantages and meritorious features of the present invention will be more fully understood from the following detailed description of the drawings and the preferred embodiment, the appended claims and the drawings, which are described briefly hereinbelow.

BRIEF DESCRIPTION OF THE DRAWINGS

FIG. 1 is a perspective view of a contoured thermal pack unit of the present invention;

FIG. 2 is a top plan view, partially broken away, of the therapeutic thermal pack unit of the preferred embodiment of the present invention;

FIG. 3 is a fragmentary, sectional, perspective side view of the therapeutic thermal pack unit of the preferred embodiment of the present invention;

FIG. 4 is a perspective view of one of the halves or sections of the pack unit of FIG. 2 showing the header portion, individualized channels and the raised portions thereabout;

FIG. 5 is a sectional perspective view of an alternate embodiment of the pack unit of the present invention wherein the channels have a generally rectangular cross-section; and FIG. 6 is a fragmentary sectional perspective view illustrating an alternate embodiment to the blind end portion of the pack unit shown in FIG. 4 which includes an intermediate header portion adjacent the blind ends of the channels.

DESCRIPTION OF THE PREFERRED EMBODIMENT

FIGS. 1 and 2 illustrate the thermal pack unit, compress or applicator 10 of the present invention. The pack unit 10 includes a first pack section or lower half 11 and a second pack section or upper half 12. In the preferred embodiment of the present invention, the first and second pack sections 11 and 12 are mirror images of one another. The two halves 11, 12 are adapted to have their opened interior facing surfaces 13 mated to one another in a face-to-face manner when the pack unit 10 is assembled such that the exterior patient-contacting surface 14 is exposed. The surface 14 is usually relatively flat for good surface (pack unit) to surface (skin) contact. Preferably, the material from which the pack unit 10 is constructed would include a thermally conductive durable plastic material such as polyvinyl which can be easily and readily formed to fit the contour of a predetermined portion of the human body and which can hold that shape for as long as desired. Any suitable plastic may be used. The present invention contemplates that the pack sections 11 and 12 may be integrally molded units although any other type of suitable manufacturing process could also be used.

As shown in FIGS. 2 and 3, the upper half 12 is fitted over the lower half 11 such that the opposing surfaces 13 mate together in a face-to-face manner with a separator or sealing sheet 17 sandwiched therebetween. In the preferred embodiment, the separator sheet is made from a suitable plastic or metal which is bendable but not too resilient so that it is capable of taking a set. Hence, the pack unit 10 can be molded to conform closely to a person's face and it will maintain this desired configuration. The pack unit 10 has a header end 15 for inputting and outputting the thermal fluid to the pack unit 10 and a closed end 16. In the preferred embodiment, the lower pack section 11 includes an input header 18 for receiving the thermal fluid from a source such as a conventional circulation pump and cooler (now shown) and the upper pack section 12 includes an output header 19 for discharging the thermal fluid from the pack unit 10 for reprocessing and recirculation.

Since the pair of opposing upper and lower pack sections 12 and 11 respectively are substantially identical, the structure of one may be used to describe either. In FIGS. 2, 3 and 4, the lower pack section 11 includes a plurality of generally parallel elongated channels 20 aligned generally along the longitudinal axis of the pack unit 10. Each of the channels 20 includes a header end portion 21, a blind end portion 22, and channel sides 23. In a first embodiment, the sides 23 are curved since the cross-sectional configuration of the channels 20 is substantially semi-circular. The sides 23 of the channels 20 rise to form lands or flat portions 24 adjacent to and between the channels 20. The upper exposed surfaces of the lands 24 are coplanar with one another and generally establish a first reference plane.

The pack section 11 also includes socket-forming sides 29 and ledges or portions 25 having generally flat surface portions for receiving the edges of the separator sheet 17 thereon. These flat portions are generally coplanar with the first previously mentioned reference plane. Similarly, a socket-like end ledge 26 integral with the continuing from the side ledges 25 is formed at the header end 15 of the pack section 11 for receiving the header end of the separator sheet 17 thereon. The flat surfaces of the end ledge 26 are generally coplanar with those of the side ledges 25 and hence with the first reference plane previously described.

A plurality of flat pedestal portions 27 which are raised above the level of the first reference plane are formed between the blind ends 22 of adjacent channels 20. A similarly raised flat annular rim portion 28 is formed about the periphery of the pack section 11 which is coplanar with the pedestals 27 is provided for matedly contacting a similar rim portion 28 of the second pack section 12 when the pack unit 10 is assembled. The pack unit 10 may be easily assembled by securing the opposing pairs of pack sections 11, 12 together with a separator sheet 17 inserted therebetween by any suitable securing and sealing means 29 such as by an appropriate adhesive or by heat-sealing the edges together, etc.

As previously described, the header end 15 includes an input header 18 and an output header 19 which are substantially identical in structure in the preferred embodiment of the present invention. Each header includes a header cavity 30 and a tube-receiving stem portion 31 extending from the header end wall. The stem 31 includes a stem opening 32 and the stem 31 is adapted to telescopically receive the end portion of an input tube 33 or output tube 46 thereover so that the end portion of the tube forms a seal against the escape of thermal fluid. This enables the thermal fluid conducted by the tube 33 to be freely transferred through the stem opening 32 and into the header cavity 30 of the lower pack section 11. Similarly with the output header 19, an output tubing 46 is sealably fitted over the stem 31 to provide for the passage of thermal fluid which has been circulated through the pack unit 10 to exit from the cavity 30 through the stem opening 32 and pass through an output tubing 46 back to a reservoir for reconditioning or the like prior to subsequent recirculation. The stems 31 may be integrally molded with the sections 11, 12 or may be inserted through apertures formed therein.

The separator sheet 17 of the preferred embodiment of the present invention is generally rectangular in shape and includes side edge portions 34, a header edge portion 35 and a distal end portion 36. The sheet 17 is adapted to be received into the socket-like interior surface opening 13 of the lower section 11 within the sheet-receiving socket provided therein as hereinafter described. The lower surface 38 of the separator sheet 17 is placed to lie generally parallel to and coplanar with the first reference plane since lower surface 38 of the sheet 17 is supported on the flat adjacent portions or lands 24 between the channels 20. The side portions 34 of the sheet 17 are snugly within the socket-forming side walls 29 upon the side ledges 25 of the lower section 11 while the header end portion 35 of the sheet 17 is snugly received upon the header end socket ledge portion 26 of the lower section 11. When the separator sheet 17 is so positioned, it lies in a plane generally parallel to the first reference plane and the upper surface 37 is spaced a predetermined distance above the level of the annular rim portion 28 of the lower pack section 11.

The separator sheet 17 must also be received into the interior facing socket opening 13 of the upper pack section 12 into which it will be similarly received upon the socket ledges 25, 26 so that as the upper pack half 12 is squeezed into contact with the lower pack section 11 and the raised annular rim portions 28 are securely sealed together as by adhesive 47, the sealing sheet 17 will be slightly compressed so as to form a fluid-tight seal about the sides 34 of the sheet and about the header end 35. The lower surface 38 of the sheet 17 will seal off the top of the elongated channels 20 of the lower pack section 11 while the upper surface 37 seals off the opened top of the elongated channels 20 of the upper pack section 12. When secured in this manner, a plurality of completely individual and separate elongated channels 20 are formed from the header cavity 30 of the input header 18 through the base portion 40 of the lower pack section 11 and then out of the blind end 22 of each of the elongated channels 20 of the lower pack section 11 and around the distal end 36 of the separator sheet 17 to be received into the blind end portion 22 of a corresponding channel 20 of the upper pack section 12 to be conducted therethrough to the header cavity 30 of the output header 19.

The lower pack section 11 has an outer cavity wall 39 which is spaced below the level of the first reference plane and a base 40 of suitable thermally conductive plastic material which is disposed between the plane of the outer cavity wall 39 and the first reference plane. The plurality of elongated channels 20 is formed in the base 40 as are the lands 24. The pedestals 27 which are disposed between adjacent blind ends 22 of channels 20 and which rise above the level of the reference plane include a flat top portion 41 which is coplanar with and merges into the plane of the flat annular rim portion 28. The raised lands 27 are actually formed as pedestals having an end face 42 which contacts the distal end 36 of the sheets 17 and side faces 43 which form the blind ends 22 of the channels 20.

FIG. 5 is a lateral cross-section of an alternate embodiment of the pack unit 10 wherein the channels 20 have a generally rectangular cross-sectional configuration.

FIG. 6 is a fragmentary sectional perspective view of yet another alternate embodiment of the pack unit 10 wherein the pedestals 27 have been eliminated and a common intermediate header 44 provided laterally across the blind ends 22 of the channels 20.

In the preferred embodiment, however, the individual elongated channels 20 are kept separate and distinct from one another to provide for a uniform temperature gradient along the length of the pack unit 10. Simultaneously, the arrangement of the present invention insures that laterally adjacent areas of the pack unit 10 are always at or substantially at the same temperature thereby avoiding temperature discontinuities between adjacent areas which result when a serpentine path is used.

In addition to providing a uniform thermal gradient along the length of the pack unit 10, the arrangement of the preferred embodiment provides a substantially constant temperature laterally across the pack unit 10 as well.

Still further, the present invention provides an arrangement whereby an almost uniform temperature may be achieved over the entire surface area of the pack unit 10. This is achieved in the following manner. As the relatively cold unused thermal fluid is inputted from the tube 33 to the input header 18, it empties into the header cavity 30 and feeds into the channels 20. since the header 30 extends across all of the channels 20, at this point all of the channels 20 are receiving thermal fluid at the same initial input temperature. All of the fluid then enters the individual channels. The fluid gradually warms as it absorbs heat from the skin area of the human subject to which it is applied so that the temperature gradually increases at a relatively uniform rate along the length of the channels 20 until the fluid reaches the blind ends 22 and passes around the distal end 36 of the separator sheet 17.

This provides a linear temperature gradient along the length of the pack unit 10. However, the individual channels 20 of the top section 12 pass immediately over the corresponding channels 20 of the lower section 11 and are separated only by the thermally conductive sheet 17. Therefore, the fluid that has rounded the turn at the blind ends 22 while it is relatively warmer than when it was fed into the input header 18, it is still cooler than it will be when it exits the output header 19. Therefore, the temperature of the fluid in the blind ends 22 of the channel 20 of the upper section 12 is cooler at the closed end 16 of the pack unit 10 and warms as it approaches the header end 15.

The fluid absorbs more heat through the separator sheet 17 and the bottom or base 40 of the lower unit 11 from the skin area of the patient to which it is applied at the blind end 16 than it does at it exits the channels 20 of the upper pack section 12 adjacent the header end 15. Therefore, the coolest portion of the return fluid in the upper channel 20 of pack section 12 reinforces the warmest of the input fluid in the lower channels 20 of the pack section, while the warmest portion of the fluid to be outputted from the upper channels 20 of the pack section 12 reinforces the coolest portion of the fluid initially inputted into the lower channels 20 of the pack section 11, thereby substantially equalizing or at least tending to equalize the temperature over the entire exterior surface area 14 of the lower pack section 11.

The method of making the therapeutic thermal pack unit 10 of the present invention contemplates the steps of forming first and second half sections which are substantial mirror images of one another each having a header portion and a plurality of elongated generally parallel channels therein and then placing a separator sheet atop the channels so that one end of the sheet forms an outer boundary of the header portion while the opposite end of the sheet terminates a predetermined distance from the ends of the channels. The other half section is then placed over the first half section with the separator sheet disposed therein so that the sheet assumes a similar position with respect to the second half section. The two sections are then secured together such that their channeled interiors are facing one another and the separator sheet is sandwiched therebetween to form a fluid type seal at the header ends of the unit and over the tops of the channels. A thermal fluid can then be fed into the header of one of the half sections which is separated from the other half by the separator sheet and caused to flow through the channels and around the blind ends thereof to make a U-turn around the distal end of the separator sheet to return through the channels of the opposite half section into its header to be outputted for recycling or the like.

With this detailed description of the specific apparatus used to illustrate the prime embodiment of the present invention and the operation thereof, and method of making same, it will be obvious to those skilled in the art that various modifications can be made in the therapeutic thermal pack unit of the present invention and the method of making same and in the materials and constructions used therein without departing from the spirit and scope of the present invention which is limited only by the appended claims.

I claim:

1. A Therapeutic thermal pack unit for maintaining a relatively constant temperature gradient over a predetermined area of the human body to which it is applied comprising a first and a second pack unit section, each of said sections having generally open interior portions adapted to be secured together in a fluid tight face-to-face manner, said first pack unit section including a plurality of elongated, substantially parallel channels, substantially flat land portions about said channels, and input header means adjacent a first end of said channels for simultaneously supplying a thermal fluid to said channels for initiating fluid flow toward the opposite ends thereof, separator sheet means adapted to be disposed upon said flat land portions so as to overlay substantially all of said plurality of parallel channels from said header means to a predetermined spaced distance from the opposite blind opposite ends of said channels to seal the top of said channels except for the uncovered blind end portions thereof, said second pack unit section including channel means and an output header disposed at the same end of said pack unit as said input header, said channel means being sealed by said separator sheet means from said output header means to a predetermined distance from the blind ends of said channels so that the thermal fluid received into said input header and passing through said plurality of parallel channels then passes around the opposite end of said separator sheet means and into the blind end of said channel means and then through said channel means and out of said output header means so as to provide a substantially constant temperature gradient along the length of said pack unit when said first and second pack unit sections are operatively secured together with said separator sheet therebetween.

2. The therapeutic thermal pack unit of claim 1 wherein said first and second pack unit sections include moldable plastic material capable of being readily conformed to fit over any surface portion of the human body to aid said pack unit in staying in place while it prevents swelling and aids healing.

3. The therapeutic thermal pack unit of claim 2 wherein said thermal fluid is at a temperature lower than body temperature thereby enabling said pack unit to be used in an area having recently undergone plastic surgery, skin grafts or the like to reduce the tendency of the skin cells to die while giving time for the new blood cells to take over and aid in the healing process.

4. The therapeutic thermal pack unit of claim 1 wherein said first and second pack unit sections are similarly configured mirror images of one another and each includes a like number of correspondingly parallel channels so that said pack unit includes a plurality of substantially parallel, upper and lower, U-shaped channels separated by said sheet means for feeding and returning said thermal fluid from said input and output header means respectively.

5. The therapeutic thermal pack unit of claim 4 wherein said channels are generally semi-circular in cross section and said flat land portions about said channel includes relatively flat surfaces establishing a first plane between adjacent channels which are adapted to receive said separating sheet means thereon, and wherein said first pack unit section has the opposite blind end portions between channels raised away from said first plane to form a second plane substantially parallel to said first plane and adapted to sealably mate with corresponding portions of said second pack unit section for individualizing said channels as they pass around the spaced end of said separator sheet means.

6. The therapeutic thermal pack unit of claim 1 wherein said pack unit includes intermediate header means at said opposite blind ends of said channels to commonly collect said thermal fluid from said plurality of substantially parallel channels of said first pack unit section and feed said commonly collected thermal fluid through said channel means of said second pack unit section of said output header means.

7. The therapeutic thermal pack unit of claim 1 wherein each of said first and second pack unit sections includes raised pedestal and rim portions about and spaced apart from said substantially flat land portions to allow sufficient space for said separator sheet means to be receivably disposed on said flat land portions between said first and second pack unit sections while enabling said pack unit sections to be retainably secured together in a sandwiched fashion with said separator sheet means therebetween in a fluid-tight manner.

8. The therapeutic pack unit of claim 4 wherein said channels are generally rectangular in cross section.

9. The therapeutic pack unit of claim 4 wherein each channel of said first pack unit section is disposed directly across said separator sheet means from a corresponding channel of said second pack unit section such that the additive thermal effect experienced by the body area over which said pack unit is disposed to a relatively uniform temperature over the entire area contacting said pack unit.

10. A method of making a therapeutic thermal pack unit capable of producing a relatively uniform, substantially linear temperature gradient along the length of said pack unit comprising the steps of providing a first pack portion with a plurality of substantially parallel grooves extending substantially the entire length thereof, said first pack portion having an input header at one end of said grooves and a closed portion at the opposite blind end thereof, placing a separator sheet over said grooves such that said sheet extends from said input header to a predetermined spaced distance from the opposite blind ends of said grooves to seal the tops of the grooves while leaving the ends open, overlying the first pack portion with a second similarly configured pack portion having an output header and similarly configured parallel grooves for conducting thermal fluid from the opposite blind ends of the grooves to the output header, securing said first pack portion, said separator sheet and said second pack portion operatively together in a fluid-tight type sandwiched manner so that a thermal fluid supplied at a predetermined initial temperature to the input header of said first pack portion will be caused to flow through said parallel grooves of said first pack portion and around the spaced end of said separator sheet and back through the parallel grooves of said second pack portion to said output header to be outputted for restoral to its desired temperature for further recycling.

* * * * *